US006387062B1

(12) United States Patent
Moore, Jr.

(10) Patent No.: US 6,387,062 B1
(45) Date of Patent: May 14, 2002

(54) APPARATUS AND METHOD FOR MASSAGING A USER'S BACK

(76) Inventor: Albert Edward Moore, Jr., 215 Grand Pre, L'Acadie, Quebec (CA), J2Y 1J6

( * ) Notice: Subject to any disclaimer, the term of this patent is extended or adjusted under 35 U.S.C. 154(b) by 0 days.

(21) Appl. No.: 09/483,285

(22) Filed: Jan. 14, 2000

Related U.S. Application Data

(60) Provisional application No. 60/116,162, filed on Jan. 15, 1999.

(51) Int. Cl.[7] .................................................. A61M 7/00
(52) U.S. Cl. .......................... 601/98; 601/101; 601/103
(58) Field of Search .............................. 601/97, 98, 99, 601/101, 102, 103, 107, 108, 111, 134

(56) References Cited

U.S. PATENT DOCUMENTS 1,276,526 A * 8/1918 Hardy et al. .................. 601/98
1,645,339 A 10/1927 Monroe
2,360,975 A 10/1944 Petersen
2,445,158 A * 7/1948 Sparhawk
2,664,882 A * 1/1954 Parker
2,773,498 A * 12/1956 Himmelman
3,656,190 A * 4/1972 Regan et al.
4,085,738 A 4/1978 Kodera
4,699,126 A 10/1987 Lancaster
5,092,315 A 3/1992 Bennett et al.
5,179,940 A * 1/1993 Barreiro ...................... 601/99
5,464,382 A 11/1995 Wang

FOREIGN PATENT DOCUMENTS

EP 0 913 142 A3 9/1998
RU 1692578 A1 11/1991
WO WO 97/37627 10/1997

* cited by examiner

*Primary Examiner*—Michael A. Brown
*Assistant Examiner*—Benjamin K. Koo
(74) *Attorney, Agent, or Firm*—Thompson Coburn LLP

(57) ABSTRACT

A massage apparatus comprises a support structure, a plurality of massaging arms operatively connected to the support structure, and an actuating mechanism. Each massaging arm has at least one massaging finger adapted to impart a massaging force to a user. Each massaging arm is moveable relative to the support structure in a manner to move its corresponding massaging finger relative to the support structure between a rearward position and a forward position. The actuating mechanism is adapted to engage the massaging arms in a manner to sequentially move the massaging fingers between their rearward and forward positions.

23 Claims, 3 Drawing Sheets

APPARATUS AND METHOD FOR MASSAGING A USER'S BACK

This application incorporates by reference and claims priority based on U.S. provisional application Ser. No. 60/116,162 having a filing date of Jan. 15, 1999.

BACKGROUND OF THE INVENTION

This invention relates to massage mechanisms of the type inserted into furniture.

Massage is an ancient art which has been practiced for centuries. Masseuses trained in different areas of massage use their fingers and hands to loosen the muscles in different parts of another's body. Masseuses usually focus on the back, neck and spinal areas, however, as the muscles here are important for maintaining posture and are frequently tight due to stress or back injuries.

As an alternative to massages by masseuses, people have used implements and devices in an effort to replicate the actions of a masseuse. Conventional devices include those that produce heat and vibrate, those with prongs to press into muscles, cushions which vibrate alternately on different areas of the back and neck, and massage mechanisms within upholstered furniture. Conventional massage devices within upholstered furniture are expensive and complex, and do not replicate the massage action of a masseuse.

SUMMARY OF THE INVENTION

Among the several advantages and features of the present invention may be noted the provision of an improved massage apparatus and an improved method for massaging a user's back; the provision of such a massage apparatus which may be incorporated into upholstered furniture; the provision of such a massage apparatus which emulates the massaging action of a masseuse; the provision of such a massage apparatus which emulates the massaging action of shiatsu massage therapy; the provision of such a massage mechanism which employs sequential contacts to cause soothing movement on the spine; the provision of such a massage apparatus which is more economical than conventional massage mechanisms; the provision of such a massage mechanism which is of generally simple construction.

Generally, a massage apparatus of the present invention comprises a support structure, a plurality of massaging arms operatively connected to the support structure, and an actuating mechanism. Each massaging arm has at least one massaging finger adapted to impart a massaging force to a user. Each massaging arm is moveable relative to the support structure in a manner to move its corresponding massaging finger relative to the support structure between a rearward position and a forward position. The actuating mechanism is adapted to engage the massaging arms in a manner to sequentially move the massaging fingers between their rearward and forward positions.

Another aspect of the present invention is a method of massaging a user's back while a user's back is in contact with a forward-facing surface of a back engaging member. The back engaging member further has a rearward-facing surface opposite the forward-facing surface. The method comprises providing a massage apparatus having an elongate support structure extending in a longitudinal direction, and a plurality of massaging arms operatively connected to the support structure. Each massaging arm has at least one massaging finger adapted to impart a massaging force to a user. The massaging arms are arranged in a longitudinal row relative to the support structure. Each massaging arm is moveable relative to the support structure in a manner to move its corresponding massaging finger relative to the support structure between a rearward position and a forward position. The method further comprises positioning the massage apparatus relative to the back engaging member in a manner so that the massaging fingers are generally adjacent the rearward facing surface of the back engaging member, and moving the massaging arms relative to the elongate support structure so that the massaging fingers sequentially move between their rearward and forward positions. The massaging fingers impart a massaging force against the user's back when the user's back is in contact with the forward-facing surface of the back engaging member as the massaging fingers move to their forward positions.

Other objects and features will be in part apparent and in part pointed out herinafter.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
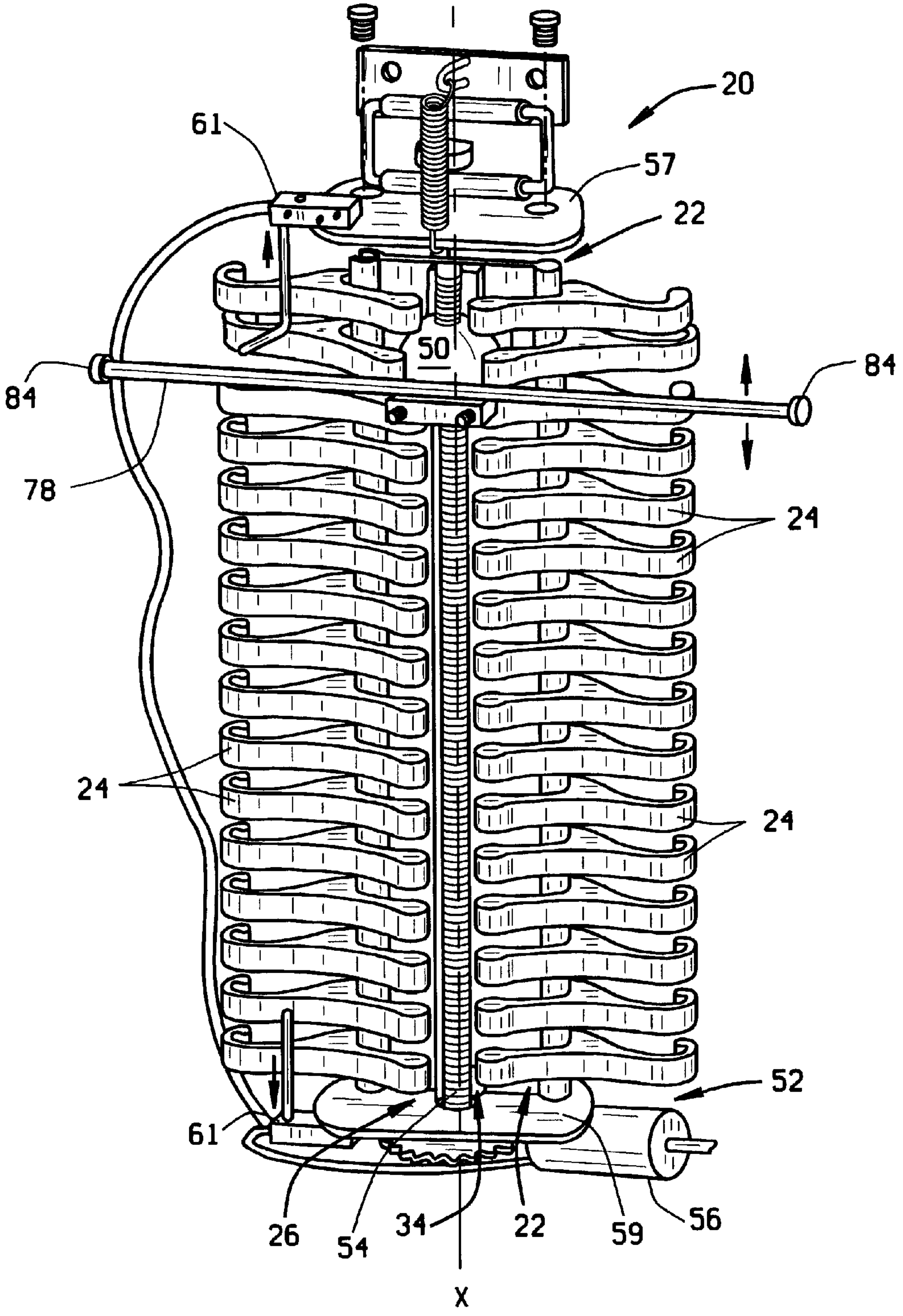
FIG. 1 is a perspective view of a massage apparatus of the present invention.

Referring now to the drawings and first more particularly to FIG. 1, a massage apparatus of the present invention is indicated in its entirety by the reference numeral 20. The massage apparatus 20 includes a support structure, generally indicated at 22, a plurality of massaging arms 24, and an actuating mechanism, generally indicated at 26.

The support structure 22 is preferably an elongate, rigid member. Preferably the support structure 22 is of aluminum and formed via an extrusion process. It preferably includes two longitudinally extending C-shaped channels 30, 32 (FIGS. 2 and 3) and a longitudinally extending central grooved channel 34.

Figure 2:
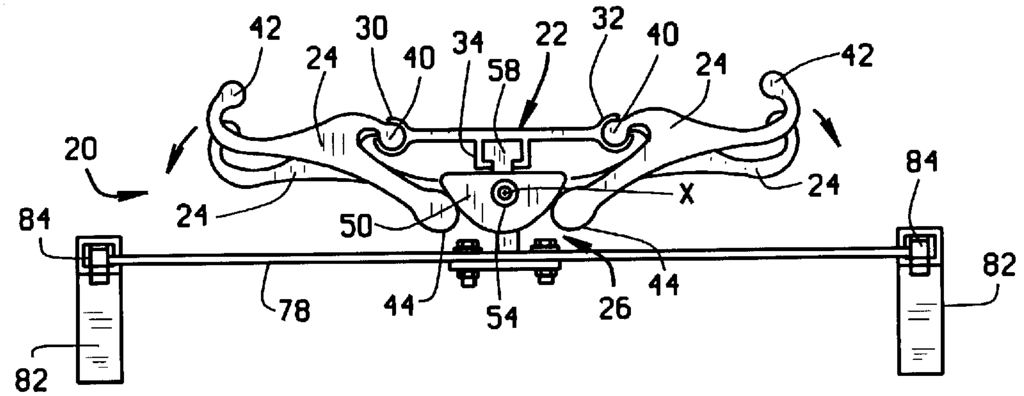
FIG. 2 is a top plan view of the massage apparatus of FIG. 1.
Figure 3:
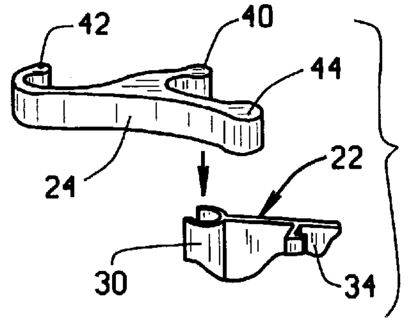
FIG. 3 is an exploded, fragmented, perspective view of a massaging arm and support structure of the massage apparatus of FIG. 1.

The massaging arms 24 are preferably of a rigid polyvinyl chloride (PVC) or rigid polypropylene. Each massaging arm 24 preferably includes a pin portion 40 at an intermediate region of the arm. The pin portion is sized and configured for insertion into one of the C-shaped channels 30, 32 for pivotal movement of the massaging arm relative to the support structure 22. The massaging arm 24 further includes a massaging finger 42 preferably at an outer end of the massaging arm, and a contacting surface 44 preferably at an inner end of the massaging arm. The massaging finger 42 is adapted to impart a massaging force to a user's back upon pivotal movement of the massaging arm 24 relative to the support structure 22. As described in greater detail below, the contacting surface 44 is engageable with the actuating mechanism to move the massaging arm 24 relative to the support structure 22. As shown in FIG. 2, each massaging arm 24 is preferably pivotal relative to the support structure via the pin portion 40 in one of the C-shaped channels 30, 32 to move the massaging finger 42 between a forward position and a rearward position. The top two massaging arms 24 shown in FIG. 2 are shown as pivoted so that their corresponding massaging fingers 42 are in their forward positions, and the lower massaging arms shown in FIG. 2 are pivoted so that their corresponding massaging fingers are in their rearward positions.

The actuating mechanism 26 preferably includes an arm engaging member 50 and a drive mechanism, generally indicated at 52 (FIG. 1), for moving the arm engaging member along a longitudinal axis X (FIGS. 1 and 2). The drive mechanism 52 preferably comprises an elongate screw 54 extending along the longitudinal axis X, and a drive motor 56 for turning the screw about the axis X. The screw 54 includes a screw thread and is journaled at its upper and lower ends to suitable brackets 57, 59 fixed to the support structure 22. The drive motor 56 is preferably a conventional, reversible, twelve volt dc motor with a worm gear head allowing for substantial torque with almost silent running. Preferably, the arm engaging member 50 comprises a cam member (also designated by reference number 50) shaped and configured for pushing against the contacting surfaces 44 of the massaging arms 24 to pivot the arms relative to the support structure 22. Preferably, the cam member 50 is of a suitable polymeric material, such as a self-lubricating nylon, and has a threaded bore (not shown) shaped and configured for meshing with the screw thread of the screw 54. The cam member 50 further includes a rectangular projection 58 (FIG. 2) shaped for a slide fit in the central channel 34 of the support structure. The cam member 50, central channel 34, screw 54, and drive motor 56 cooperate so that turning of the screw causes the cam member 50 to move up and down along the axis X. Preferably, the actuating mechanism 26 further includes limit switches 61 (FIG. 1) at the top and bottom brackets 57, 59 to stop and reverse current when the cam reaches its limits to reverse the motor and reverse the turning direction of the screw.

As shown in FIG. 2, the massaging arms 24 are preferably arranged into two opposing, side-by-side, stacked rows. The cam member 50 is preferably eye-shaped in order to start the pivoting action of a pair of massaging arms 24 slowly and gently and to finish in a similar fashion just as the next pair of massaging arms are activated. In operation, the drive motor 56 is energized to turn the screw 54 which causes the cam member 50 to move longitudinally up or down along the axis X. As the cam member 50 moves along the axis X, it pushes against the contacting surfaces 44 of a pair of the massaging arms 24 (i.e., one massaging arm of one row and one massaging arm of the other row) to pivot the arms 24 about their pin portions to thereby move the massaging fingers from their rearward positions to their forward positions. The pivotal movement of each arm is in a plane perpendicular to the axis X. Also, because of the configuration of the arms 24 and the support structure 22, the arms do not move longitudinally relative to the screw. In other words, the massaging arms 24 are connected to the support structure 22 in a manner for preventing longitudinal movement (i.e., up and down movement as shown in FIG. 1) relative to the screw. Up and down movement of the cam member 50 sequentially (or serially) actuates the arms 24 to sequentially pivot the arms to sequentially move the massaging fingers between their rearward and forward positions. Preferably, as the cam member moves up the screw, the lower-most pair of arms 24 are first engaged by the cam member and pivoted thereby. As the cam member 50 continues to move up the screw, it then engages the next to lower-most pair of arms and thereby pivots them. Preferably, the cam member 50 and massaging arms 24 are sized and shaped so that no more than one massaging finger in any row is pivoted to its forward position (i.e., fully extended by the cam member) at a given time.

Although the arm engaging member 50 has been described as being a cam member for imparting a cam action on the massaging arms 24, it is to be understood that other constructions could be employed without departing from the scope of this invention. For example, the arm engaging member could be configured with gear teeth on its external surface which intermesh with gear teeth on the massaging arms to sequentially pivot the massaging arms as the arm engaging member is raised or lowered by rotation of the screw. Also, although the massaging arms have been described as being pivotally connected to the support structure, it is to be understood that other types of connections are possible without departing from the scope of this invention. For example, the massaging arms could be fixed to the support structure but be formed with a flex joint which allows the massaging arm to bend. Also, although the cam member preferably moves along the support structure in a linear motion, it is to be understood that the cam member could be adapted to allow for a threaded insert to move in and out within the cam member as the cam member follows a shaped central extrusion even though the threaded rod remains straight.

Figure 5:
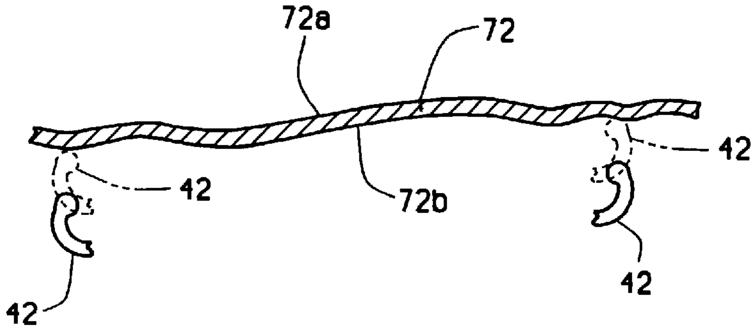
FIG. 5 is a fragmented, section view showing massaging arms of the massage apparatus of FIG. 4 adjacent a back engaging member (e.g., the upholstered surface) of the chair.
Figure 4:
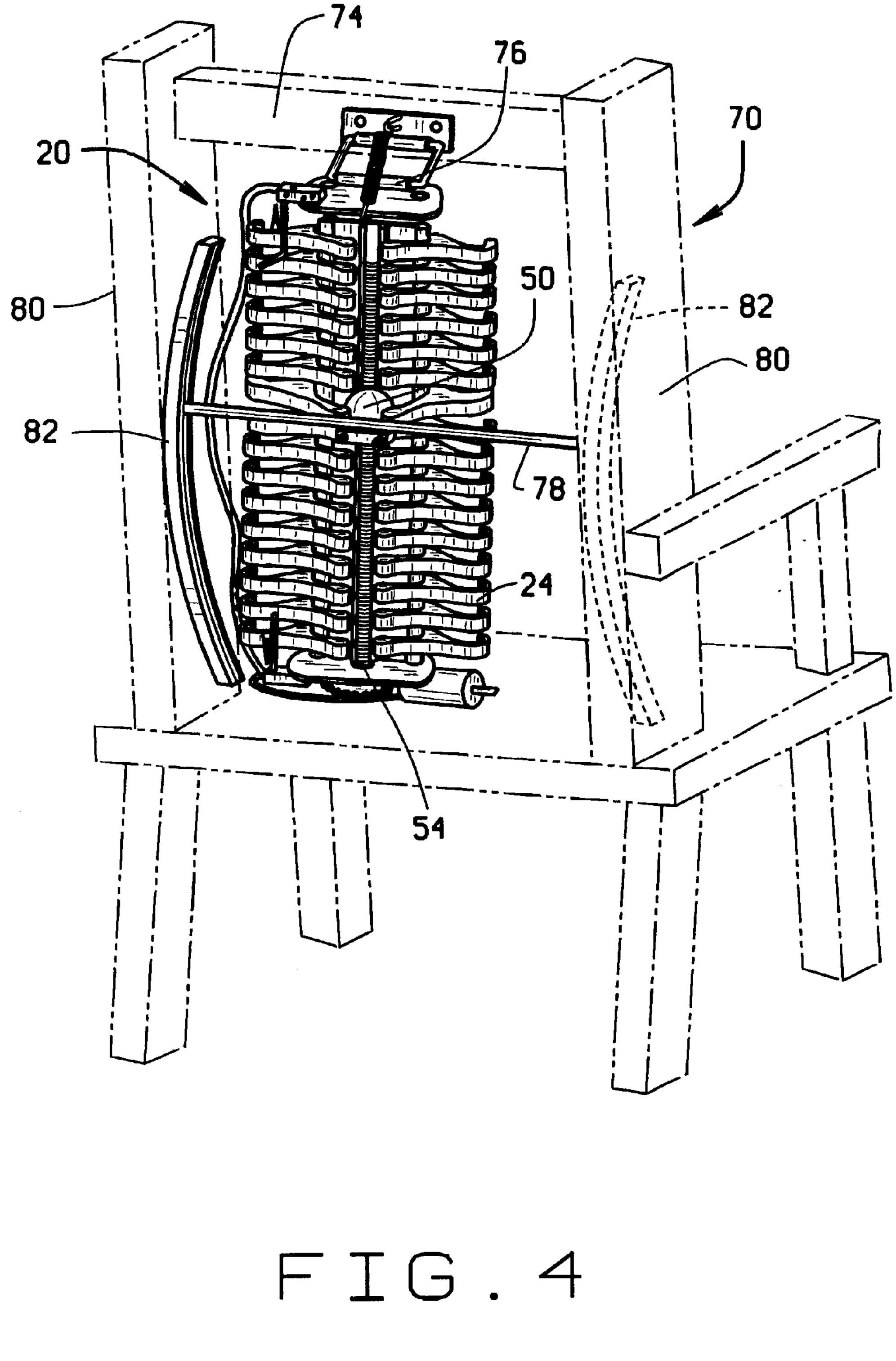
FIG. 4 is a perspective view showing the massage apparatus of FIG. 1 as a a component in a chair, the chair being shown only schematically to show detail of the massage apparatus.

Referring now to FIG. 4, the massage apparatus 20 is shown as part of an article of furniture, and more particularly is shown as part of a chair, generally indicated at 70. The chair 70 enables a massage to be performed while a user is seated on the chair with his or her back contacting a forward-facing surface 72*a* of a back engaging member 72 (FIG. 5) of the chair (e.g., the upholstered surface of the chair). Referring to FIG. 5, the massaging fingers 42 sequentially press against a rearward-facing surface 72B of the back engaging member 72 to impart massaging forces up and down the user's back on opposite sides of the user's spine. The massaging fingers 42 are shown in solid in their rearward positions and shown in phantom in their forward positions. Preferably, the support structure 22 is approximately the same length as that of the back of a typical adult user. Also preferably, a sufficient number of massaging arms 24 are pivotally attached to the support structure 22 to enable the massage apparatus 20 to massage the entire length of the user's back. Preferably, the massage apparatus 20 has two rows of massaging arms 24, with each row preferably having at least ten massaging arms, and more preferably having at least fifteen massaging arms.

As shown in FIG. 4, the upper portion of the massage apparatus 20 is pivotally connected to an upper frame member 74 of the chair 70 via a hinge 76. A generally horizontal rod 78 spans side frame members 80 of the chair 70 and is secured to the cam member 50. The horizontal rod 78 has rollers 84 (FIG. 1) on its ends which ride in curved tracks 82 fixed to the side frame members 80. As the cam member 50 moves up and down the screw 54, the rollers 84 at the ends of the horizontal rod 78 ride in the curved tracks 82 to pivot the massage apparatus 20 via the hinge 76. The cam member 50 follows the path of the curved tracks 82 to produce an appropriate massage pressure profile on the user's back.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A massage apparatus comprising:

a support structure;

a plurality of massaging arms operatively connected to the support structure, each massaging arm having at least one massaging finger adapted to impart a massaging force to a user, each massaging arm being moveable relative to the support structure in a manner to move its corresponding massaging finger relative to the support structure between a rearward position and a forward position, the massaging arms being arranged as two longitudinal side-by-side rows, one of the rows constituting a left longitudinal row and the other row constituting a right longitudinal row, the left row comprising a first plurality of the massaging arms and the right row comprising a second plurality of the massaging arms, the massaging arms being pivotally connected to the support structure for pivotal movement of the massaging arms between their rearward and forward positions;

an actuating mechanism adapted to engage the massaging arms in a manner to sequentially move the massaging fingers between their rearward and forward positions; and wherein the actuating mechanism comprises an arm engaging member and a drive mechanism for moving the arm engaging member along a longitudinal axis, the arm engaging member and the massaging arms being adapted and arranged so that movement of the arm engaging member along the longitudinal axis causes the arm engaging member to sequentially engage the massaging arms in a manner to sequentially move the massaging fingers between their rearward and forward positions.

2. A massage apparatus as set forth in claim 1 wherein the massaging arms and actuating mechanism are adapted so that movement of the arm engaging member along the longitudinal axis causes the arm engaging member to sequentially engage the massaging arms in a manner to move the massaging fingers in a planar movement between their rearward and forward positions.

3. A massage apparatus as set forth in claim 1 wherein each massaging arm comprises a cam surface, and wherein the arm engaging member comprises a cam member engageable with the cam surfaces of the massaging arms, the cam member and the cam surfaces being adapted so that movement of the cam member along the longitudinal axis causes the cam member to sequentially engage the cam surfaces of the massaging arms in a manner to sequentially move the massaging fingers between their rearward and forward positions.

4. A massage apparatus as set forth in claim 1 wherein the drive mechanism comprises an elongate screw and a motor for turning the screw about the longitudinal axis, the screw having a screw thread, the arm engageable member being operatively engageable with the screw thread in a manner so that turning of the screw about the longitudinal axis moves the arm engageable member longitudinally along the longitudinal axis.

5. A massage apparatus as set forth in claim 4 wherein the massaging arms are connected to the support structure in a manner for preventing longitudinal movement of the massaging arms relative to the screw.

6. A massage apparatus as set forth in claim 1 wherein the massaging arms are operatively connected to the support structure in a manner for preventing longitudinal movement of the massaging arms relative to the support structure.

7. A method comprising:

providing a massage apparatus as set forth in claim 6, the actuating mechanism comprising an arm engaging member adapted to engage the massaging arms in a manner to move the massaging fingers between their rearward and forward positions; and moving the arm engaging member along a curved path in a manner to cause the arm engaging member to sequentially engage the massaging arms to thereby sequentially move the massaging fingers between their rearward and forward positions.

8. A massage apparatus as set forth in claim 1 wherein the massaging apparatus is configured and adapted such that the arm engaging member moves along a curved path as it moves along the longitudinal axis.

9. A method of massaging a user's back while a user's back is in contact with a forward-facing surface of a back engaging member, the back engaging member further having a rearward-facing surface opposite the forward-facing surface, the method comprising:

providing a massage apparatus having an elongate support structure extending in a longitudinal direction, and a plurality of massaging fingers operatively connected to the support structure, each massaging finger being adapted to impart a massaging force to a user, the massaging fingers being arranged as two side-by-side finger rows, one of the finger rows constituting a left finger row and the other finger row constituting a right finger row, the left finger row constituting a first plurality of the massaging fingers and the right finger row constituting a second plurality of the massaging fingers, each massaging finger being moveable relative to the support structure between a rearward position and a forward position;

positioning the massage apparatus relative to the back engaging member in a manner so that the massaging fingers are generally adjacent the rearward facing surface of the back engaging member;

moving the massaging fingers of the left finger row between their rearward and forward positions in a sequential manner so that each of the massaging fingers of the left finger row moves along an arcuate path from its rearward position to its forward position at a time different than when the other massaging fingers of the left finger row are moved from their rearward positions to their forward positions, the massaging fingers of the left finger row imparting a massaging force against the user's back when the user's back is in contact with the forward-facing surface of the back engaging member as the massaging fingers of the left finger row move to their forward positions;

moving the massaging fingers of the right finger row between their rearward and forward positions in a sequential manner so that each of the massaging fingers of the right finger row moves along an arcuate path from its rearward position to its forward position at a time different than when the other massaging fingers of the right finger row are moved from their rearward positions to their forward positions, the massaging fingers of the right finger row imparting a massaging force against the user's back when the user's back is in contact with the forward-facing surface of the back engaging member as the massaging fingers of the right finger row move to their forward positions, the step of moving the massaging fingers of the right finger row occurring concurrently with the step of moving the massaging fingers of the left finger row.

10. A method as set forth in claim 9 wherein:

the step of moving the massaging fingers of the left finger row comprises moving each massaging finger of the left finger row between its rearward and forward positions independent of the movement of the other massaging fingers of the left finger row between their rearward and forward positions; and the step of moving the massaging fingers of the right finger row comprises moving each massaging finger of the right finger row between its rearward and forward positions independent of the movement of the other massaging fingers of the right finger row between their rearward and forward positions.

11. A method as set forth in claim 9 further comprising a plurality of massaging arms, each massaging finger being a portion of one of the massaging arms, the massaging arms being operatively connected to the support structure in a manner for preventing longitudinal movement of the massaging arms relative to the support structure.

12. A method as set forth in claim 11 wherein the support structure extends generally along a longitudinal axis and wherein each massaging arm is operatively connected to the support structure for movement in a plane generally perpendicular to the longitudinal axis, the steps of moving the massaging fingers comprising moving the massaging fingers in planes which are generally perpendicular to the longitudinal axis.

13. A method as set forth in claim 9 wherein:

the step of moving the massaging fingers of the left finger row causes the massaging fingers of the left finger row to impart a massaging force against a left region of the user's back; and the step of moving the massaging fingers of the right finger row causes the massaging fingers of the right finger row to impart a massaging force against a right region of the user's back.

14. An article of furniture having a back-engageable surface adapted to engage a user's back, the article of furniture further comprising a massage apparatus adjacent the back-engageable surface, the massage apparatus comprising:

a support structure;

a plurality of massaging fingers operatively connected to the support structure, each massaging finger being adapted to impart a massaging force to a user, each massaging finger being moveable relative to the support structure between a rearward position and a forward position, the massaging fingers being arranged as two side-by-side finger rows, one of the finger rows constituting a left finger row and the other finger row constituting a right finger row, the left finger row comprising a first plurality of the massaging fingers and the right finger row comprising a second plurality of the massaging fingers; and an actuating mechanism adapted to sequentially move the massaging fingers of the left finger row between their rearward and forward positions, and simultaneously to sequentially move the massaging fingers of the right finger row between their rearward and forward positions;

the massage apparatus being operable to massage the user's back when the user's back is in engagement with the back-engaging surface and when the actuating mechanism is operated to move the massaging fingers between their rearward and forward positions:

the article of furniture further comprises a furniture frame member, the support structure of the massage apparatus being operatively connected to the furniture frame member, the article of furniture further comprising a hinge mechanism for moving the support structure relative to the furniture frame member.

15. An article of furniture as set forth in claim 14 wherein the back-engageable surface comprises a surface of a chair.

16. An article of furniture as set forth in claim 14 wherein the massage apparatus is configured such that operation of the actuating mechanism in a manner to sequentially move the massaging fingers between their rearward and forward positions causes movement of the support structure relative to the furniture frame member.

17. A massage apparatus comprising:

a support structure;

a plurality of massaging fingers operatively connected to the support structure, each massaging finger being adapted to impart a massaging force to a user, each massaging finger being moveable relative to the support structure between a rearward position and a forward position, the massaging fingers being arranged as two side-by-side finger rows, one of the finger rows constituting a left finger row and the other finger row constituting a right finger row, the left finger row comprising a first plurality of the massaging fingers and the right finger row comprising a second plurality of the massaging fingers; and an actuating mechanism adapted to sequentially move the massaging fingers of the left finger row between their rearward and forward positions, the actuating mechanism comprising a moveable member moveable between raised and lowered positions, the actuating mechanism being configured and adapted to move the moveable member along a curved path from its raised position to its lowered position, the actuating mechanism being adapted and configured such that moving the moveable member along the curved path causes the massaging fingers of the left finger row to sequentially move between their rearward and forward positions and causes the massaging fingers of the right finger row to sequentially move between their rearward and forward positions.

18. A massaging apparatus as set forth in claim 17 wherein the left finger row constitutes a longitudinal left finger row and the right finger row constitutes a longitudinal right finger row, and wherein the massaging fingers are operatively connected to the support structure in a manner for preventing longitudinal movement of the massaging fingers relative to the support structure.

19. A massage apparatus comprising:

a support structure;

a plurality of massaging arms operatively connected to the support structure, each massaging arm being moveable relative to the support structure between a forward position and a rearward position, each massaging arm being adapted to impart a massaging force to a user as the massaging arm is moved from its rearward position to its forward position, the plurality of massaging arms being arranged as a longitudinal row;

an actuating mechanism comprising an arm engaging member and a drive mechanism for longitudinally moving the arm engaging member relative to the massaging arms between a lower position and an upper position;

the arm engaging member and the massaging arms being adapted and arranged such that longitudinal movement of the arm engaging member relative to the massaging arms causes the arm engaging member to sequentially engage the massaging arms in a manner to sequentially move the massaging arms between their forward and rearward positions;

the massaging apparatus being configured and adapted such that the arm engaging member moves along a curve as it moves between its upper and lower positions.

20. A massage apparatus as set forth in claim 19 wherein the curve extends from the lower position to the upper position.

21. A massage apparatus as set forth in claim 19 wherein:

the row of massaging arms comprises at least a first massaging arm, a second massaging arm and a third massaging arm;

the massaging apparatus is configured and arranged so that movement of the arm engaging member to a first position moves the first massaging arm to its forward position, the massaging apparatus is configured and arranged so that movement of the arm engaging member to a second position moves the second massaging arm to its forward position, and the massaging apparatus is configured and arranged so that movement of the arm engaging member to a third position moves the second massaging arm to its forward position; and the first position is longitudinally spaced from the second and third positions and the second position is longitudinally spaced from the third position.

22. A massage apparatus as set forth in claim 21 wherein the second position is laterally spaced from a line intersecting the first and third positions.

23. A massage apparatus as set forth in claim 19 wherein the arm engaging member is shaped and adapted so that no more than one massaging arm of the row is moved to its forward position at a given time.

* * * * *